United States Patent

Julius

[11] Patent Number: 5,859,250
[45] Date of Patent: Jan. 12, 1999

[54] PREPARATION OF 4-AMINO-2,2,6,6-TETRAMETHYLPIPERIDINE (TAD) VIA 2,2,6,6-TETRAMETHYL-4-[(2,2,6,6-TETRAMETHYL-4-PIPERIDYLIDENE) AMINO]PIPERIDINE AS INTERMEDIATE

[75] Inventor: Manfred Julius, Limburgerhof, Germany

[73] Assignee: BASF Aktiengesellschaft, Ludwigshafen, Germany

[21] Appl. No.: 959,165

[22] Filed: Oct. 28, 1997

[30] Foreign Application Priority Data

Oct. 28, 1996 [DE] Germany ............... 196 44 770.4

[51] Int. Cl.⁶ ................................................ C07D 211/56
[52] U.S. Cl. .................................... 546/244; 546/186
[58] Field of Search .................................. 546/186, 244

[56] References Cited

U.S. PATENT DOCUMENTS 4,923,992  5/1990  Vignali et al. ................. 546/186
5,693,817  12/1997  Frentzen et al. .............. 546/244

FOREIGN PATENT DOCUMENTS 033 529   8/1981   European Pat. Off. .
336 895   10/1989  European Pat. Off. .
714 890   9/1995   European Pat. Off. .
3525387   7/1985   Germany .
2176473   12/1996  United Kingdom .

*Primary Examiner*—Alan L. Rotman
*Assistant Examiner*—Charandit S. Aulakh
*Attorney, Agent, or Firm*—Keil & Weinkauf

[57] ABSTRACT

A description is given, as an alternative to known processes, of a process for preparing 4-amino-2,2,6,6-tetramethylpiperidine (TAD) of the formula (I)

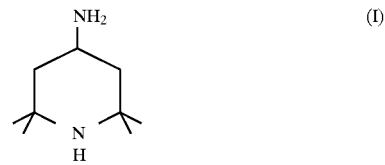

TAD which comprises the steps of reacting without catalysis, in a first step, 2,2,6,6-tetramethylpiperidine-4-one(TAA) of the formula II

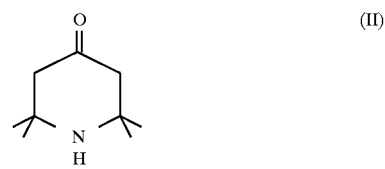

TAA with TAD to form 2,2,6,6-tetramethyl4[(2,2,6,6tetramethyl-4-piperidylidene)- amino]piperidine (imine III) of the formula III below

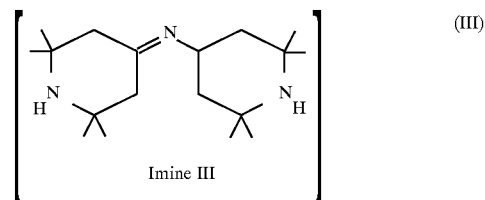

Imine III and of reacting, in a further step, the imine (III) with ammonia and hydrogen in the presence of a hydrogenation catalyst to give 2 mol equivalents of TAD.

5 Claims, No Drawings

PREPARATION OF 4-AMINO-2,2,6,6-TETRAMETHYLPIPERIDINE (TAD) VIA 2,2,6,6-TETRAMETHYL-4-[(2,2,6,6-TETRAMETHYL-4-PIPERIDYLIDENE)AMINO]PIPERIDINE AS INTERMEDIATE

The invention relates to a process for preparing 4-amino-2,2,6,6-tetramethylpiperidine (TAD) via 2,2,6,6-tetramethyl-4-[(2,2,6,6-tetramethyl-4-piperidylidine)-amino]-piperidine as intermediate.

4-amino-2,2,6,6-tetramethylpiperidine(triacetondiamine, TAD) is a key intermediate for the synthesis of light stabilizers of the HALS type (HALS=H indered A mine L ight S tabilizer). These play an important part as additives for the stabilization of synthetic polymers such as polyolefins, for example. It is known that synthetic polymers undergo more or less severe chemical or physical changes under the influence of sunlight or ultraviolet radiation from other sources. In order to prevent or to retard this deleterious effect of ultraviolet radiation on synthetic polymers, appropriate light stabilizers, for instance of the abovementioned HALS type, are added to the polymers.

EP-A 0 033 529 discloses a process for preparing 4-amino-2,2,6,6-tetramethylpiperidine (TAD) in which 2,2,6,6-tetramethylpiperidine-4-one (TAA) is treated with ammonia and hydrogen in the presence of hydrogenation catalysts at from 120° to 220° C. under a pressure in the range from 150 to 500 bar. However, TAA reacts sensitively to $O_2$ or air, leading to colored impurities. These impurities arise again in the products after the abovementioned process has been carried out, or have to be separated off for preparation of the light stabilizers.

Consequently, a description is now given, as an alternative to the known process, of a process for preparing 4-amino-2,2,6,6-tetramethylpiperidine (TAD) of the formula (I)

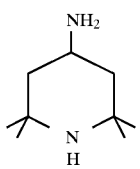

TAD which comprises the steps of reacting, in a first step, 2,2,6,6-tetramethylpiperidine-4-one(TAA) of the formula II

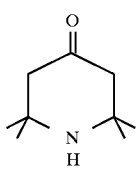

TAA with TAD to form 2,2,6,6-tetramethyl-4-[(2,2,6,6-tetramethyl-4-piperidylidene)-amino]piperidine (imine III) of the formula III below

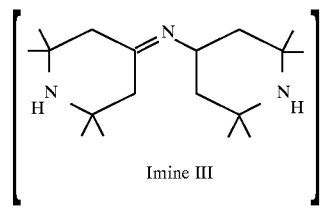

Imine III and of reacting, in a further step, the imine (III) with ammonia and hydrogen in the presence of a hydrogenation catalyst to give 2 mol equivalents of TAD.

Furthermore, the invention provides a process for preparing 2,2,6,6-tetramethyl-4-[(2,2,6,6-tetramethyl-4-piperidylidene)amino] piperidine of the above-mentioned formula III which comprises the step of reacting 2,2,6,6-tetramethylpiperidine-4-one (TAA) of the formula II below

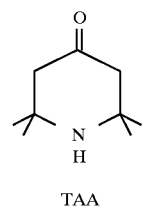

TAA with 4-amino-2,2,6,6-tetramethylpiperidine(TAD) of the formula I.

In a further embodiment of the invention, TAD is prepared by the former process but without the reaction step of TAA with TAD, from the imine III, the latter being reacted with ammonia and hydrogen in the presence of a hydrogenation catalyst to give 2 mol equivalents of TAD.

It has been found in accordance with the invention that TAA can be reacted with TAD with elimination of water to form the imine (III). In this way the imine III can be prepared with high selectivity and in a good yield.

The TAD is prepared subsequently by an aminating hydrogenation over a hydrogenation catalyst, which likewise proceeds with very high selectivity and with almost complete conversion. In this way, the novel process uses one mol equivalent each of TAA and TAD to obtain two mol equivalents of TAD.

The various novel embodiments of the process are illustrated by way of example by the following equation:

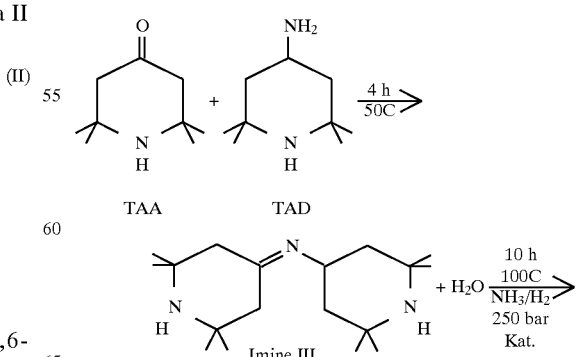

-continued

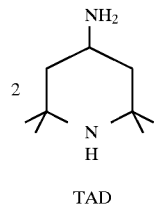

TAD

The above-illustrated condensation of TAA with TAD to form the imine (III) preferably takes place without catalysis and at from 30° to 90° C.

A very particular advantage of the novel process is that it can be carried out in a one-stage procedure. In this procedure the imine obtained as intermediate is not isolated as an independent substance but instead can be subjected directly to aminating hydrogenation under customary conditions, for example at 100° C., with 250 bar of $H_2$ and with excess $NH_3$ to give TAD.

In addition, the process is preferably carried out without additional solvent. Moreover, it can be conducted either batchwise in an autoclave, for example over a customary commercial suspended or fixed-bed catalyst, or continuously in a tubular reactor, for example over a fixed-bed catalyst. Preferred hydrogenation catalysts comprise Ni and Co.

The novel process is illustrated by the following examples:

EXAMPLE 1

Synthesis of 4-amino-2,2,6,6-tetramethylpiperidine (TAD) A 1.2 l HC autoclave with a gasifying stirrer was charged with 85.95 g (0.55 mol) of TAD purity by GC: 98.8 area-%), 77.62 g (0.50 mol) of TAA (purity by GC: 99.8 area-%) and 50 g of Raney cobalt. After blanketing with $N_2$ the mixture was heated to 50° C. and stirred for 4 h under the autogenous pressure. The reaction mixture then had the following approximate composition (area-% by GC): 15.8% TAA, 8.5% TAD, 72.5% imine III, 3.2% remainder (GC conditions: capillary column 30 m RTX-5 amines; 50 °–250° C., 5° C./min.). The contents of the autoclave were cooled to room temperature (in the course of which the reaction mixture solidified), 170 g (10.0 mol) of liquid ammonia were injected, and the mixture was heated to 100° C. The pressure was raised with hydrogen to 250 bar, while stirring, and the batch was run at 100° C. for 10 h while injecting 250 bar each hour. A total of about 15 bar of $H_2$ were taken up.

After the autoclave had been cooled and let down, the reaction product was dissolved in 225 g of methanol and the catalyst was separated off by decantation. Concentration at 40° C. under 5 mbar gave 157 g of crude liquid product The conversion based on imine III was 99.4% with a selectivity of 98.5%. The yield of TAD based on BAA employed was 65.3 g (0.42 mol, 84%).

EXAMPLE 2

Synthesis of 2,2,6,6-tetramethyl-4-[(2,2,6,6-tetramethyl-4-piperidylidene)amino]-piperidine (imine III) A stirred flask was charged under $N_2$ with 85.95 g (0.55 mol) of TAD and 77.62 g (0.50 mol) of BAA and the mixture was heated at 50° C. for 4 h. According to GC the reaction mixture then had the following composition (area-%): 15.76% BAA, 8.47% TAD, 72.46% imine III, 3.31% remainder (GC conditions: capillary column 30 m RTX-5 amines; 50°–250° C./min.). This corresponds to a selectivity for the formation of the imine of 95.6% at a conversion of 75.8%.

The pure, white imine was obtained by crystallization from petroleum ether 30/75. m.p.: 59°–61° C.

Elemental analysis:

|  | C | H | N |  |
| --- | --- | --- | --- | --- |
| % calc. | 73.66 | 12.02 | 14.32 | $C_{18}H_{35}N_3$ |
| % found | 73.3 | 12.1 | 14.2 | (MW = 293.50) |

$^{13}$C-NMR (62.9 MHz, CDCl$_3$): δ=28.76 (2CH$_3$), 31.45 (2CH$_3$), 31.87 (2CH$_3$), 35.06 (2CH$_3$), 42.11 (CH$_2$–CH), 46.05 (2CH$_2$—C=N), 50.51, (2C(CH$_3$)$_2$), 51.40 (C(CH$_3$)$_2$), 52.26 (C(CH$_3$)$_2$), 53.72 (CH—N=C), 54.07 (CH$_2$—CH), 168.28 (C=N) Mass spectrum (EI): M$^+$=293. IR spectrum: 1650 cm$^{-1}$ (C=N).

I claim:

1. A process for preparing 4-amino-2,2,6,6-tetramethylpiperidine (TAD) without catalysis of the formula I

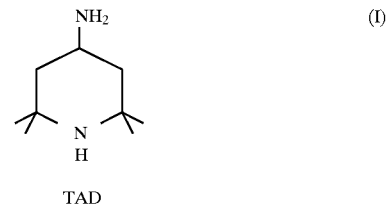

TAD which comprises the steps of reacting
in a first step, 2,2,6,6-tetramethyl-piperidine-4-one(TAA) of the formula

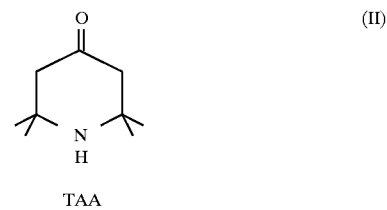

TAA with TAD to form 2,2,6,6-tetramnethyl-4-[(2,2,6,6-tetramethyl-4-piperidylidene)amino]piperidine (imine III) of the formula III below

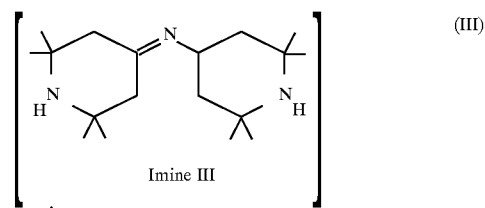

Imine III and of reacting
in a further step, the imine (III) with ammonia and hydrogen in the
presence of a hydrogenation catalyst to give 2 mol equivalents of TAD.

2. The process of claim 1, wherein the further process step of reacting the imine (III) with ammonia and hydrogen in the presence of a hydrogenation catalyst is carried out directly after the first process step.

3. A process as defined in claim 1, wherein the further process step of reacting the imine (III) with ammonia and hydrogen is carried out at from 20° to 150° C. and under a pressure of from 50 to 300 bar in the absence of solvents.

4. A process for preparing 2,2,6,6,-tetranethyl-4-piperidine of the formula III below

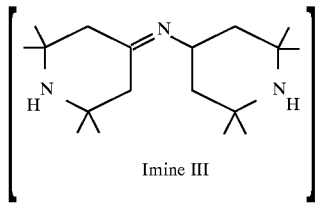

Imine III (III)

which comprises the step of reacting without catalysis 2,2,6,6-tetramethylpiperidin-4-one (TAA) of the formula II below

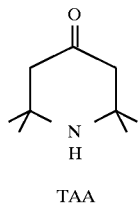

TAA (II)

with amino-2,2,6,6-tetramethylpiperidine (TAD) of the formula I

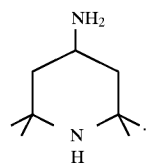

TAD (I)

5. A process for preparing TAD of the formula I

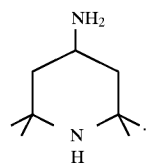

TAD (I)

which comprises reacting an imine of the formula III

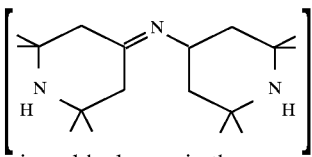

(III)

with ammonia and hydrogen in the presence of a hydrogenation catalyst.

* * * * *

UNITED STATES PATENT AND TRADEMARK OFFICE
CERTIFICATE OF CORRECTION

PATENT NO. : 5,859,250
DATED : January 12, 1999
INVENTOR(S) : Manfred JULIUS

It is certified that error appears in the above-identified patent and that said Letters Patent is hereby corrected as shown below:

Col. 5, claim 4, line 1, "2,2,6,6,-tetranethyl-4-" should be
--2,2,6,6-tetramethyl-4-[(2,2,6,6-tetramethyl-4-piperidylidene)amino]--.

Col. 5, claim 4, line 29, "with amino-" should be --with 4-amino- --.

Signed and Sealed this

Twenty-ninth Day of June, 1999

Attest:

Q. TODD DICKINSON

*Attesting Officer*   Acting Commissioner of Patents and Trademarks